(12) United States Patent
Ellson

(10) Patent No.: US 6,806,051 B2
(45) Date of Patent: *Oct. 19, 2004

(54) ARRAYS OF PARTIALLY NONHYBRIDIZING OLIGONUCLEOTIDES AND PREPARATION THEREOF USING FOCUSED ACOUSTIC ENERGY

(75) Inventor: Richard N. Ellson, Palo Alto, CA (US)

(73) Assignee: Picoliter Inc., Sunnyvale, CA (US)

(*) Notice: Subject to any disclaimer, the term of this patent is extended or adjusted under 35 U.S.C. 154(b) by 20 days.

This patent is subject to a terminal disclaimer.

(21) Appl. No.: 09/962,731

(22) Filed: Sep. 24, 2001

(65) Prior Publication Data

US 2002/0042077 A1 Apr. 11, 2002

Related U.S. Application Data

(63) Continuation-in-part of application No. 09/669,267, filed on Sep. 25, 2000, now abandoned.

(51) Int. Cl.[7] ............ C12Q 1/68; C12P 19/34; C12M 1/34; C07H 21/02; C07H 21/04
(52) U.S. Cl. .......... 435/6; 435/7.1; 435/91.1; 435/91.2; 435/287.2; 530/22.1; 530/23.1; 530/24.3; 530/24.31; 530/24.32; 530/24.33
(58) Field of Search .......... 435/6, 7.1, 91.1, 435/91.2, 287.2; 536/6, 21, 911, 91.2, 287.2

(56) References Cited

U.S. PATENT DOCUMENTS

| | | | |
|---|---|---|---|
| 4,308,547 A | 12/1981 | Lovelady et al. |
| 4,500,707 A | 2/1985 | Caruthers et al. |
| 4,697,195 A | 9/1987 | Quate et al. |
| 4,719,476 A | 1/1988 | Elrod et al. |
| 4,751,529 A | 6/1988 | Elrod et al. |
| 4,751,530 A | 6/1988 | Elrod et al. |

(List continued on next page.)

FOREIGN PATENT DOCUMENTS

| | | |
|---|---|---|
| EP | 0067597 A1 | 12/1982 |
| WO | WO 92/06103 | 4/1992 |
| WO | WO 93/20092 | 10/1993 |
| WO | WO9411530 | * 5/1994 |
| WO | WO 02/20537 | 3/2002 |
| WO | WO 02/20541 | 3/2002 |

OTHER PUBLICATIONS

Hardy et al. (1994), "Reagents for the Preparation of Two Oligonicleotides Per Synthesis (TOPS™)," *Nucleic Acids Research* 22(15):2998–3004.

(List continued on next page.)

*Primary Examiner*—Jeffrey Siew
(74) *Attorney, Agent, or Firm*—Reed & Eberle LLP; Dianne E. Reed; Karen Canaan (57) ABSTRACT

Partially nonhybridizing oligonucleotides are provided that contain two or more hybridizing segments, with any two hybridizing segments separated by a nonhybridizing spacer segment, i.e., a nucleotidic or nonnucleotidic segment that has little or no likelihood of binding to an oligonucleotide sequence found in nature. Oligonucleotide arrays are also provided in which at least one of the oligonucleotides of the array is a partially nonhybridizing oligonucleotide. The partially nonhybridizing oligonucleotides serve as multifunctional probes wherein each hybridizing segment of a single partially nonhybridizing oligonucleotide serves as an individual probe. Also provided are methods for preparing and using the partially nonhybridizing oligonucleotides and arrays formed therewith. A particularly preferred method of array fabrication involves the use of focused acoustic energy.

38 Claims, 1 Drawing Sheet

U.S. PATENT DOCUMENTS

| | | | |
|---|---|---|---|
| 4,751,534 A | | 6/1988 | Elrod et al. |
| 4,797,693 A | | 1/1989 | Quate |
| 4,801,953 A | | 1/1989 | Quate |
| 5,256,535 A | | 10/1993 | Ylikoski et al. |
| 5,405,783 A | | 4/1995 | Pirrung et al. |
| 5,424,186 A | | 6/1995 | Fodor et al. |
| 5,436,327 A | | 7/1995 | Southern et al. |
| 5,445,934 A | | 8/1995 | Fodor et al. |
| 5,489,678 A | | 2/1996 | Fodor et al. |
| 5,622,822 A | | 4/1997 | Ekeze et al. |
| 5,631,134 A | | 5/1997 | Cantor |
| 5,635,352 A | * | 6/1997 | Urdea et al. ................ 435/6 |
| 5,700,637 A | | 12/1997 | Southern et al. |
| 5,736,327 A | | 4/1998 | Collins |
| 5,744,305 A | | 4/1998 | Fodor et al. |
| 5,795,714 A | | 8/1998 | Cantor et al. |
| 5,798,779 A | | 8/1998 | Nakayasu et al. |
| 5,837,832 A | | 11/1998 | Chee et al. |
| 6,007,987 A | | 12/1999 | Cantor et al. |
| 6,015,880 A | | 1/2000 | Baldeschwieler et al. |
| 6,028,189 A | | 2/2000 | Blanchard |
| 6,029,896 A | | 2/2000 | Self et al. |
| 6,057,100 A | | 5/2000 | Heyneker |
| 6,087,112 A | | 7/2000 | Dale |
| 6,136,962 A | | 10/2000 | Shi et al. |
| 6,309,822 B1 | * | 10/2001 | Fodor et al. ................ 435/6 |
| 6,322,971 B1 | * | 11/2001 | Chetverin et al. ............ 435/6 |
| 6,355,431 B1 | * | 3/2002 | Chee et al. ................ 435/6 |
| 2002/0037579 A1 | | 3/2002 | Ellson et al. |
| 2002/0061258 A1 | | 5/2002 | Mutz et al. |
| 2002/0061598 A1 | | 5/2002 | Mutz et al. |

OTHER PUBLICATIONS

Pon et al. (2001), "Multiple Oligonucleotide Synthesis in Tandem on Solid–Phase Supports for Small and Large Scale Synthesis," *Nucleosides, Nucleotides & Necleic Acids* *20*(4–7):985–989.

U.S. patent application Ser. No. 09/669,996, Ellson et al., filed Sep. 25, 2000.

Theriault et al. (1999), "Application of Ink–Jet Printing Technology to the Manufacture of Molecular Arrays," DNA Microarrays: A Practical Approach, Ed. M. Schena, Chapter 6 (Oxford University Press).

U.S. patent application Ser. No. 09/669,996, Ellson et al., filed Sep. 25, 2000.

* cited by examiner

ARRAYS OF PARTIALLY NONHYBRIDIZING OLIGONUCLEOTIDES AND PREPARATION THEREOF USING FOCUSED ACOUSTIC ENERGY

CROSS-REFERENCE TO RELATED APPLICATIONS

This is a continuation-in-part of U.S. patent application Ser. No. 09/669,267, filed Sep. 25, 2000 now abandoned, the disclosure of which is incorporated by reference herein.

TECHNICAL FIELD

This invention relates generally to oligonucleotides and oligonucleotide arrays. More particularly, the invention pertains to arrays of oligonucleotides containing nonhybridizing segments, and to methods for preparing and using such arrays.

BACKGROUND

Nucleic acid hybridization is a known method for identifying specific sequences of nucleic acids. Hybridization is based upon pairing between complementary nucleic acid strands. Single-stranded oligonucleotides having known sequences can be used as probes to identify target sequences of nucleic acid analytes, by exposing the probes to sample solutions containing nucleic acid analytes of interest. If a nucleic acid analyte hybridizes to a probe, the analyte necessarily contains the target sequence. Various aspects of this method have been studied in detail. In essence, all variations allow complementary base sequences to pair and form double-stranded molecules, and a number of methods are known in the art to determine whether pairing has occurred, such as those described in U.S. Pat. No. 5,622,822 to Ekeze et al. and U.S. Pat. No. 5,256,535 to Ylikoski et al.

High density arrays of oligonucleotides are now known and commercially available for a number of purposes. These so-called "DNA chips" or "gene chips" can be used, for example, in gene expression analysis and mutation detection, polymorphism analysis, mapping, evolutionary studies, and other applications. It has recently become possible to provide single chips that represent the entire human genome. Microfabricated arrays have primarily been manufactured using photolithography, piezoelectric technology technologies, and mechanical spotting. The photolithography approach makes use of semiconductor processing techniques wherein masks are used to selectively irradiate and thus activate modified nucleoside phosphoramidites in the stepwise synthesis of oligonucleotides. See, for example, U.S. Pat. Nos. 5,424,186, 5,445,934, 5,489,678 and 5,744,305 to Fodor et al. and U.S. Pat. No. 5,405,783 to Pirrung et al. With the piezoelectric approach, nucleoside monomers or oligonucleotide segments are delivered to a substrate surface using noncontact inkjet printing technology, i.e., ejected from individual nozzles onto specific sites on a substrate surface; see, for example, U.S. Pat. No. 6,015,880 to Baldeschwieler et al. Microspotting involves direct surface contact wherein microspotting pins, capillaries or tweezers are used to transfer intact biomolecules onto a solid surface.

Each of the aforementioned techniques provides an oligonucleotide array in which the oligonucleotides are intended to serve as hybridization probes, with each oligonucleotide generally intended to bind to at most one complementary oligonucleotide segment. If an array probe were used as a multifunctional probe, i.e., capable of hybridizing to two or more complementary oligonucleotide segments, there would be no means for isolating regions where hybridization is desired from regions where it is not. Thus, known arrays of oligonucleotide probes are limited in this respect.

Accordingly, there is a need in the art for more versatile oligonucleotide arrays wherein the individual oligonucleotides of the array can be used as multifunctional probes, in turn substantially enhancing the utility of a single array.

SUMMARY OF THE INVENTION

It is thus a primary object of the invention to address the above-mentioned need in the art by providing partially nonhybridizing oligonucleotides useful as multifunctional probes in an oligonucleotide array.

It is another object of the invention to provide oligonucleotide arrays wherein at least one of the oligonucleotides is a partially nonhybridizing oligonucleotide comprised of two discrete hybridizing segments with a nonhybridizing spacer segment therebetween.

It is another object of the invention to provide oligonucleotide arrays wherein at least one of the oligonucleotides is a partially nonhybridizing oligonucleotide comprised of a plurality of hybridizing oligonucleotide segments, with any two such segments separated by a nonhybridizing spacer segment.

It is still another object of the invention to provide such arrays wherein the nonhybridizing spacer segment is a nucleotidic or nonnucleotidic segment that has little or no likelihood of binding to an oligonucleotide sequence found in nature.

It is yet another object of the invention to provide a method for fabricated oligonucleotides containing one or more partially nonhybridizing oligonucleotides as above, the method comprising attaching pre-synthesized oligonucleotides to designated sites on a substrate surface.

It is a further object of the invention to provide a method for fabricated oligonucleotides containing one or more partially nonhybridizing oligonucleotides as above, the method comprising successively coupling individual nucleotidic monomers and/or oligonucleotide segments to a each of a plurality of designated sites on a substrate surface.

It is an additional object of the invention to provide such a method wherein the pre-synthesized oligonucleotides, nucleotidic monomers and/or oligonucleotide segments are applied to the designated sites on a substrate surface using focused acoustic energy.

It is still an additional object of the invention to provide a method of using an array of oligonucleotides as described herein in a hybridization assay.

Additional objects, advantages and novel features of the invention will be set forth in part in the description which follows, and in part will become apparent to those skilled in the art upon examination of the following, or may be learned by practice of the invention.

In one aspect of the invention, then, an oligonucleotide array is provided that is comprised of a plurality of oligonucleotides attached to a substrate surface, wherein at least one of the oligonucleotides is a partially nonhybridizing oligonucleotide comprised of two or more discrete hybridizing segments with a nonhybridizing spacer segment separating any two hybridizing segments. The hybridizing segments are generally oligonucleotide segments approximately 8 to 400 nucleotides in length, preferably in the range of approximately 16 to 80 nucleotides in length. The nonhybridizing spacer segments may be nucleotidic or nonnucleotidic, although nucleotidic spacer segments are preferred. Nucleotidic spacer segments include, by way of example, oligomeric segments comprised of a recurring single nucleotide, e.g., $(A)_n$, $(T)_n$, $(G)_n$ or $(C)_n$ wherein n is an integer in the range of about 9 to 50, preferably about 9 to 20. Within any given partially nonhybridizing oligonucleotide, the hybridizing segments may be the same or different; in either case, it is possible to use a single partially nonhybridizing oligonucleotide as a multifunctional probe by virtue of containing more than one hybridizing oligonucleotide segment.

In another aspect, a multilayer oligonucleotide array is provided comprised of a plurality of identical partially nonhybridizing oligonucleotides, each of which has the formula wherein SS is a substrate surface, L is a linking moiety, $X^1$, $X^2$ and $X^3$ are hybridizing oligonucleotide segments, $Y_1$ and $Y^2$ are nonhybridizing spacer segments, m is zero or 1, and n is an integer in the range of zero to 50, wherein each nonhybridizing spacer segment $Y^i$ of each oligonucleotide is covalently linked to the corresponding nonhybridizing spacer segment $Y^i$ of at least one adjacent oligonucleotide through a linking moiety containing a cleavable site, and further wherein with any one partially nonhybridizing oligonucleotide, (a) the hybridizing segments may be the same or different, and (b) if more than one nonhybridizing segment is present, the nonhybridizing segments may be the same or different. In this way, a ladder-type structure is provided with two or more layers of hybridizing array segments, whereby the upper array may be used first and the uppermost linking moiety then cleaved to expose the next array, and so forth. Each "array" layer may the same as the others, or each array layer may be different.

Methods for using these oligonucleotide arrays in hybridization assays are also provided. By virtue of the partially nonhybridizing oligonucleotide probes, each of which acts as a multifunctional probe, the oligonucleotide arrays have substantially enhanced utility and versatility in any of a variety of hybridization assay formats.

The invention also provides a method for fabricated oligonucleotide arrays containing at least one partially nonhybridizing oligonucleotide as described above. The method may comprise "spotting" intact oligonucleotides onto designated sites of a substrate surface, or it may comprise in situ synthesis of oligonucleotides by individually coupling individual nucleotidic monomers and/or oligonucleotide segments (e.g., the nonhybridizing segments) at designated sites on a substrate surface. A particularly preferred fabrication method involves the use of focused acoustic energy, wherein an acoustic ejector is used to eject single, extremely small droplets of nucleotide-containing or oligonucleotide-containing fluids from fluid reservoirs (e.g., individual wells in a well plate) onto designated sites of a substrate surface.

BRIEF DESCRIPTION OF THE DRAWINGS

FIGS. 1 and 2 schematically illustrate in simplified cross-sectional view the operation of a focused acoustic ejection device in the preparation of oligonucleotide arrays.

DESCRIPTION OF THE INVENTION

Before describing the present invention in detail, it is to be understood that unless otherwise indicated this invention is not limited to specific oligonucleotides, hybridizing segments, nonhybridizing segments, array preparation methods, supports, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, the term "an oligonucleotide" is intended to mean a single oligonucleotide or two or more oligonucleotides that may be the same or different, "a hybridizing segment" is intended to mean one or more hybridizing segments, and the like.

In describing and claiming the present invention, the following terminology will be used in accordance with the definitions set out below.

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Suitable analogs will be known to those skilled in the art and are described in the pertinent texts and literature. Common analogs include, but are not limited to, 1-methyladenine, 2-methyladenine, $N^6$-methyladenine, $N^6$-isopentyl-adenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromo-guanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methyl-aminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "oligonucleotide" shall be generic to polydeoxyribo-nucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones, providing that the polymers contain nucleobases in a configuration that allows for base pairing and base stacking, such as is found in DNA and RNA. Thus, these terms include known types of oligonucleotide modifications, for example, substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the terms "polynucleotide" and "oligonucleotide," and these terms will be used interchangeably. These terms refer only to the primary structure of the molecule. As used herein the symbols for nucleotides and polynucleotides are according to the IUPAC-IUB Commission of Biochemical Nomenclature recommendations (*Biochemistry* 9:4022, 1970).

The term "probe" is used herein to indicate an oligonucleotide or an oligonucleotide segment capable of hybridizing with an oligonucleotide or oligonucleotide segment containing a nucleic acid sequence complementary to a nucleic acid sequence in the probe.

The term "array" as used herein refers to a two-dimensional arrangement of features such as an arrangement of oligonucleotide probes on a substrate surface. Arrays are generally comprised of regular, ordered features, as in, for example, a rectilinear grid, parallel stripes, spirals, and the like, but non-ordered arrays may be advantageously used as well. An array differs from a "pattern" in that patterns do not necessarily contain regular and ordered features. The present arrays have no optical significance to the unaided human eye; for example, the invention does not involve printing on paper or other substrates in order to form letters, numbers, bar codes, figures, or other inscriptions. The arrays prepared using the method of the invention generally comprise in the range of about 4 to about 10,000,000 features, more typically about 4 to about 1,000,000 features.

The term "attached," as in, for example, a substrate surface having an oligonucleotide "attached" thereto, includes covalent binding, adsorption, and physical immobilization. The terms "binding" and "bound" are identical in meaning to the term "attached."

The term "adsorb" as used herein refers to the noncovalent retention of a molecule by a substrate surface. That is, adsorption occurs as a result of noncovalent interaction between a substrate surface and adsorbing moieties present on the molecule that is adsorbed. Adsorption may occur through hydrogen bonding, van der Waal's forces, polar attraction or electrostatic forces (i.e., through ionic bonding). Examples of adsorbing moieties include, but are not limited to, amine groups, carboxylic acid moieties, hydroxyl groups, nitroso groups, sulfones and the like. Unless otherwise specified, hybridization is distinct from adsorption.

The term "sample" as used herein relates to a material or mixture of materials, typically, although not necessarily, in fluid form, containing one or more components of interest.

By "protecting group" as used herein is meant a species that prevents a segment of a molecule from undergoing a specific chemical reaction, but is removable from the molecule following completion of that reaction. This is in contrast to a "capping group," which permanently binds to a segment of a molecule to prevent any further chemical transformation of that segment.

The term "fluid" as used herein refers to matter that is nonsolid or at least partially gaseous and/or liquid. A fluid may contain a solid that is minimally, partially or fully solvated, dispersed or suspended. Examples of fluids include, without limitation, aqueous liquids (including water per se and buffered water), nonaqueous liquids such as organic solvents and lipidic liquids, supercritical fluids, gases, and the like. As used herein, the term "fluid" is not synonymous with the term "ink" in that an ink must contain a colorant and may not be gaseous.

The term "near" is used to refer to the distance from the focal point of the focused acoustic radiation to the surface of the fluid from which a droplet is to be ejected. The distance should be such that the focused acoustic radiation directed into the fluid results in droplet ejection from the fluid surface, and one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

The terms "focusing means" and "acoustic focusing means" as used herein refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and described, for example, in U.S. Pat. No. 5,798,779 to Nakayasu et al. and Amemiya et al. (1997) *Proceedings of the* 1997 *IS&T NIP*13 *International Conference on Digital Printing Technologies Proceedings*, at pp. 698–702.

The term "reservoir" as used herein refers a receptacle or chamber for holding or containing a fluid. Thus, a fluid in a reservoir necessarily has a free surface, i.e., a surface that allows a droplet to be ejected therefrom.

The term "substrate" as used herein refers to any material having a surface onto which one or more fluids may be deposited. The substrate may be constructed in any of a number of forms such as wafers, slides, well plates, membranes, for example. In addition, the substrate may be porous or nonporous as may be required for deposition of a particular fluid. Suitable substrate materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like.

Substrates of particular interest are porous, and include, as alluded to above: uncoated porous glass slides, including CPG slides; porous glass slides coated with a polymeric coating, e.g., an aminosilane or poly-L-lysine coating, thus having a porous polymeric surface; and nonporous glass slides coated with a porous coating. The porous coating may be a porous polymer coating, such as may be comprised of a cellulosic polymer (e.g., nitrocellulose) or polyacrylamide, or a porous metallic coating (for example, comprised of microporous aluminum). Examples of commercially available substrates having porous surfaces include the Fluorescent Array Surface Technology (FAST™) slides available from Schleicher & Schuell, Inc., which are coated with a 10–30 μm thick porous, fluid-permeable nitrocellulose layer that substantially increases the available binding area per unit area of surface. Other commercially available porous substrates include the completely permeable slides currently available from Eppendorf, and substrates having "three-dimensional" geometry, by virtue of an ordered, highly porous structure that enables reagents to flow into and penetrate through the pores and channels of the entire structure. Such substrates are available from Gene Logic, Inc. under the tradename "Flow-Thru Chip," and are described by Steel et al. in Chapter 5 of *Microarray Biochip Technology* (BioTechniques Books, Natick, Mass., 2000).

The term "porous" as in a "porous substrate" or a "substrate having a porous surface," refers to a substrate or surface, respectively, having a porosity (void percentage) in the range of about 1% to about 99%, preferably about 5% to about 99%, more preferably in the range of about 15% to about 95%, and an average pore size of about 100 Å to about 1 mm, typically about 500 Å to about 0.5 mm.

The term "impermeable" is used in the conventional sense to mean not permitting water or other fluid to pass through. The term "permeable" as used herein means not "impermeable." Thus, a "permeable substrate" and a "substrate having a permeable surface" refer to a substrate or surface, respectively, which can be permeated with water or other fluid.

While the foregoing support materials are representative of conventionally used substrates, it is to be understood that a substrate may in fact comprise any biological, nonbiological, organic and/or inorganic material, and may be in any of a variety of physical forms, e.g., particles, strands, precipitates, gels, sheets, tubing, spheres, containers, capillaries, pads, slices, films, plates, and the like, and may further have any desired shape, such as a disc, square, sphere, circle, etc. The substrate surface may or may not be flat, e.g., the surface may contain raised or depressed regions. A substrate may additionally contain or be derivatized to contain reactive functionalities that covalently link a compound to the substrate surface. These are widely known and include, for example, silicon dioxide supports containing reactive Si—OH groups, polyacrylamide supports, polystyrene supports, polyethylene glycol supports, and the like.

The term "surface modification" as used herein refers to the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

The term "substantially" as in, for example, the phrase "substantially all oligonucleotides of an array," refers to at least 90%, preferably at least 95%, more preferably at least 99%, and most preferably at least 99.9%, of the oligonucleotides of an array. Other uses of the term "substantially" involve an analogous definition.

"Optional" or "optionally" means that the subsequently described circumstance may or may not occur, so that the description includes instances where the circumstance occurs and instances where it does not. For example, the phrase "optional additional hybridizing segment" means that an additional hybridizing segment may or may not be present, and, thus, the description includes oligonucleotides wherein the additional hybridizing segment is present and oligonucleotides wherein the additional hybridizing segment is not present.

In one embodiment, then, the invention pertains to oligonucleotides having alternating hybridizing segments and nonhybridizing segments, i.e., oligonucleotides containing at least two segments capable of hybridizing to complementary oligonucleotide segments, with nonhybridizing spacer segments separating each hybridizing segment from adjacent hybridizing segment(s). The oligonucleotide is attached at one terminus to the surface of a substrate, typically a solid support as is conventionally used in solid phase hybridization assays. The nonhybridizing segments provide for increased specificity and selectivity when the oligonucleotide is used as a hybridization probe, in that complementary oligonucleotide segments will be less likely to bind to adjacent hybridizing segments. Furthermore, each such oligonucleotide—referred to herein as a "partially nonhybridizing oligonucleotide" by virtue of the nonhybridizing segment or segments—can be used as a multifunctional probe, with each hybridizing segment designed to hybridize to different nucleic acid sequences. However, the invention is not limited in this regard, and in some cases it may be necessary or desirable for each hybridizing segment of a single partially nonhybridizing oligonucleotide to be the same.

The partially nonhybridizing oligonucleotide may be covalently attached to a substrate, typically although not necessarily through linker moieties as is known in the art. Alternatively, the partially nonhybridizing oligonucleotide may be attached to the substrate through noncovalent interaction, e.g., by an ionic bonding, hydrogen bonding, adsorption or physical immobilization; again, a linker may or may not be present. A linker, if present, should have a length sufficient to allow an oligonucleotide analyte to bind to the hybridizing segment closest to the substrate. The linker may contain a cleavable site to allow release of the oligonucleotide from the substrate surface after use, i.e., after completion of a hybridization assay. Cleavable sites may be restriction sites (i.e., sites cleavable by restriction endonucleases), or they may be chemically, thermally or photolytically cleavable sites, as will be appreciated by those of ordinary skill in the art.

Regardless of the type of attachment and the presence or absence of a linker, the substrate that is used to bind the partially nonhybridizing oligonucleotide is comprised of a material that has a plurality of reactive sites on its surface, or is treated or coated so as to have a plurality of reactive sites on its surface. The reactive sites are typically hydrophilic moieties such as hydroxyl groups, carboxyl groups, thiol groups, and/or substituted or unsubstituted amino groups, although, preferably, the reactive hydrophilic moieties are hydroxyl groups. Suitable substrate materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose), metallic compounds (particularly microporous aluminum), or the like. While the foregoing support materials are representative of conventionally used substrates, it is to be understood that the substrate may in fact comprise any biological, nonbiological, organic and/or inorganic material, and may be in any of a variety of physical forms, e.g., particles, strands, precipitates, gels, sheets, tubing, spheres, containers, capillaries, pads, slices, films, plates, slides, and the like, and may further have any desired shape, such as a disc, square, sphere, circle, etc. The substrate surface may or may not be flat, e.g., the surface may contain raised or depressed regions. Generally, the partially nonhybridizing oligonucleotide is linked to the support, optionally via a linker, through its 3'-hydroxyl group, although in some cases the linkage may be through its 5'-hydroxyl group.

The hybridizing segments of the partially nonhybridizing oligonucleotide are comprised of single-stranded oligonucleotide segments that are capable of hybridizing to a complementary oligonucleotide segment, e.g., in an oligonucleotide analyte. Each hybridizing segment is preferably although not necessarily in the range of approximately 8 to 400 nucleotides in length, more preferably in the range of approximately 16 to 80 nucleotides in length. Each hybridizing segment thus acts as an individual probe, so that a single partially nonhybridizing oligonucleotide is functionally equivalent to a plurality of probes. Thus, when these oligonucleotides are bound to a substrate in an ordered oligonucleotide array with a single oligonucleotide at each locus of the array, the density of the oligonucleotides can be reduced by a factor equivalent to the number of hybridizing segments in each partially nonhybridizing oligonucleotide. Alternatively, the density of oligonucleotides per unit of surface area may be unchanged, with the effective probe density—i.e., the density of hybridizing oligonucleotide segments/unit surface area—increasing by a factor equivalent to the number of hybridizing segments in each partially nonhybridizing oligonucleotide.

The nonhybridizing spacer segment or segments of the partially nonhybridizing oligonucleotide may comprise any molecular moiety that is incapable of or highly unlikely to hybridize to an oligonucleotide sequence found in nature. Generally, a "nonhybridizing" segment has an equilibrium binding constant of less than or equal to 1% of the binding constant of hybridizing segments. The nonhybridizing spacer segment may be nonnucleotidic, e.g., a hydrocarbylene linkage optionally substituted with one or more nonhydrocarbyl groups and/or containing one or more heteroatoms. For example, alkylene or oxyalkylene (e.g., polyethylene glycol) linkages containing in the range of about 5 to 50 carbon atoms, preferably about 10 to 25 carbon atoms, will suffice. It is preferred, however, that the nonhybridizing spacer segments comprise nonhybridizing nucleotidic segments. Such segments include, by way of example, sequences of a single repeated nucleotide such as $(A)_n$, $(T)_n$, $(C)_n$, $(G)_n$ or $(N)_n$ wherein n is in the range of approximately 9 to 50, preferably in the range of approximately 9 to 20, and N is a nonnaturally occurring nucleotide or a modified naturally occurring nucleotide as defined earlier herein. If the spacing between hybridizing sites is made large enough, sophisticated confocal microscopy may be used to distinguish between a fluorescent signal resulting from hybridization near the substrate surface and a fluorescent signal resulting from hybridization sites distant from the surface.

Nonhybridizing nucleotidic segments also include, for example, the twelve-nucleotide sequence corresponding to the four codons for start-stop-start-stop or stop-start-stop-start. Suitable nonhybridizing nucleotidic segments can be identified by those of ordinary skill in the art by forming a histogram of all n-mer sequences ("n" may be, for example, in the range of 9 to 12) found in existing sequenced genomes, i.e., containing all possible n-mer sequences, and then verifying that a proposed nonhybridizing nucleotidic segment has low or no binding affinity for any of the sequences of the histogram. Verification may be conducted by physical hybridization or via simulation based on molecular modeling methods known to those skilled in the art, or using a combination of experimentation and simulation. For example, the BLAST ("Basic Local Alignment Search Tool") program available from the National Center for Biotechnology Information in Bethesda, Md. may be used to confirm that a proposed nonhybridizing nucleotidic segment does not bear any substantial similarity to any known naturally occurring nucleic acid sequences.

In a preferred embodiment, an oligonucleotide array is provided wherein a plurality of oligonucleotides is attached to a substrate surface in ordered fashion, with one oligonucleotide at each of a plurality of loci within the array. At least one of the oligonucleotides within the array is a partially nonhybridizing oligonucleotide as described above. Preferably, the array contains a plurality of partially nonhybridizing oligonucleotides, and more preferably the array is completely composed of partially nonhybridizing oligonucleotides, each of which has the formula $$SS\text{-}(L)_m\text{-}X^1\text{-}Y^1\text{-}X^2\text{-}(Y^2\text{-}X^3)$$

wherein SS is a substrate surface, L is a linking moiety, $X^1$, $X^2$ and $X^3$ are hybridizing oligonucleotide segments, $Y^1$ and $Y^2$ are nonhybridizing spacer segments, m is zero or 1, and n is an integer in the range of zero to approximately 50. If n is greater than 1, the $X^3$ segments may the same or different, as is also the case for the $Y^2$ segments.

The partially nonhybridizing oligonucleotide may also include one or more selectably cleavable sites. Such sites enable one to sever the oligonucleotide backbone at a predetermined locus, a feature that is useful in a variety of hybridization assay formats. A selectably cleavable site may be incorporated within a hybridizing segment, within a nonhybridizing segment, between a hybridizing segment and a nonhybridizing segment, within the linking moiety, between the oligonucleotide and the linking moiety, or between the linking moiety and the substrate surface. Selectably cleavable sites may be enzymatically, chemically, thermally or photolytically cleavable, as described in U.S. Pat. Nos. 4,775,619, 5,118,605, 5,258,506, 5,367,066, 5,380, 833, 5,580,731 and 5,591,584. As explained in the aforementioned patents, a number of reagents and methods may be used to create sites that are cleavable using chemical reagents, restriction enzymes or photolysis. See, for example, U.S. Pat. No. 5,258,506 to Urdea et al., entitled "Photolabile Reagents for Incorporation into Oligonucleotide Chains"; U.S. Pat. No. 5,367,066 to Urdea et al., entitled "Oligonucleotides with Selectably Cleavable and/or Abasic Sites"; U.S. Pat. No. 5,380,833 to Urdea, entitled "Polynucleotide Reagents Containing Selectable Cleavage Sites"; U.S. Pat. No. 5,430,136 to Urdea et al., entitled "Oligonucleotides Having Selectably Cleavable And/or Abasic Sites"; U.S. Pat. No. 5,552,538 to Urdea et al., entitled "Oligonucleotides with Cleavable Sites"; and U.S. Pat. No. 5,578,717 to Urdea et al., entitled "Nucleotides for Introducing Selectable Cleavable and/or Abasic Sites into Oligonucleotides."

The oligonucleotide array may be prepared using now-conventional techniques known to those skilled in the art of nucleic acid chemistry and/or described in the pertinent literature and texts. See, for example, *DNA Microarrays: A Practical Approach*, M. Schena, Ed. (Oxford University Press, 1999). For example, the array oligonucleotides, including or wholly comprised of partially nonhybridizing oligonucleotides, may be synthesized prior to attachment to a substrate surface and then "spotted" onto a particular locus on the surface in a manner that allows attachment thereto. Alternatively, the oligonucleotides of the array may be simultaneously synthesized in situ in a stepwise fashion by successively coupling individual nucleotidic monomers and/or oligonucleotide segments to a plurality of support-bound initial nucleotidic monomers. In one embodiment, the array oligonucleotides are synthesized in situ by successive coupling of nucleotidic monomers to form the hybridizing segments, with the nonhybridizing spacer segments formed by coupling intact, pre-synthesized nonhybridizing segments at the desired locations. The individual coupling reactions are conducted under standard conditions used for the synthesis of oligonucleotides and conventionally employed with automated oligonucleotide synthesizers. Such methodology will be known to those skilled in the art and is described in the pertinent texts and literature, e.g., in D. M. Matteuci et al. (1980) *Tet. Lett.* 521:719, U.S. Pat. No. 4,500,707 to Caruthers et al., and U.S. Pat. Nos. 5,436,327 and 5,700,637 to Southern et al.

A particularly preferred method for preparing the present oligonucleotide arrays involves the use of focused acoustic energy as described in detail in co-pending patent application U.S. Ser. No. 09/669,996 ("Acoustic Ejection of Fluids From a Plurality of Reservoirs"), inventors Ellson, Foote and Mutz, filed Sep. 25, 2000 and assigned to Picoliter, Inc. (Mountain View, Calif.). As explained in the aforementioned patent application, focused acoustic energy may be used to eject single fluid droplets from the free surface of a fluid (e.g., in a reservoir or well plate) toward designated sites on a substrate surface, enabling extraordinarily accurate and repeatable droplet deposition and allowing biomolecular arrays to be formed in high yield having densities similar to or better than those achievable using photolithographic or other techniques. A preferred system employs a single acoustic ejector, which provides improved control over droplet size, velocity, and directionality as compared with designs using a plurality of ejectors.

As described in the above-referenced patent application, the use of focused acoustic energy (FAE) to prepare oligonucleotide arrays employs a plurality of reservoirs, each adapted to contain a fluid, an acoustic ejector comprising an acoustic radiation generator and a focusing means, and a means for positioning the ejector in acoustic coupling relationship to each of the reservoirs. When the oligonucleotide arrays are synthesized by spotting intact, pre-synthesized oligonucleotides onto a solid substrate, the fluid in each reservoir will accordingly contain a pre-synthesized oligonucleotide. When the oligonucleotide arrays are synthesized in situ by coupling individual nucleoside monomers or oligonucleotide segments (e.g., the nonhybridizing segments) to designated sites on a substrate surface, the fluid in each reservoir will contain the appropriate nucleoside monomer or oligonucleotide segment.

Generally the oligonucleotide arrays will have a density in the range of approximately 10 to approximately 250,000 different oligonucleotides per square centimeter of substrate surface, typically in the range of approximately 400 to approximately 100,000 oligonucleotides molecules per square centimeter of substrate surface. However, it must be emphasized that the use of focused acoustic energy enables the preparation of far higher density arrays as well, i.e., arrays comprised of at least about 1,000,000 oligonucleotides per square centimeter of substrate surface, or even in the range of about 1,500,000 to 4,000,000 oligonucleotides per square centimeter of substrate surface. These high density arrays may be prepared on nonporous surfaces, although a significant advantage of using focused acoustic energy technology in the manufacture of arrays is that substrates with porous surfaces, and even permeable surfaces, may be used. Prior array fabrication methods have not enabled preparation of high density arrays on porous or permeable surfaces because prior spotting processes are nowhere near as accurate as the present acoustic deposition method, and prior processes have also required larger droplet volumes. Accordingly, prior array fabrication methods have been limited to the preparation of low density arrays on porous surfaces, or higher density arrays on nonporous surfaces. See, for example, U.S. Pat. No. 6,054,270 to Southern. In contrast to prior methods of manufacturing arrays, then, acoustic ejection enables highly accurate deposition of extraordinarily small liquid droplets, such that diffusion of a deposited droplet into neighboring cells is not a problem, and extraordinarily high probe densities can now be achieved with high porosity, permeable surfaces. More specifically, acoustic ejection can be used to manufacture high density arrays that can be read with a high precision digitizing scanner capable of 2 $\mu$m resolution, by depositing droplets having a volume on the order of 1 pL, resulting in deposited spots about 18 $\mu$m in diameter. For ultra-high density arrays, a smaller droplet volume is necessary, typically less than about 0.3 pL (deposition of droplets having a volume on the order of 0.25 pL will result in deposited spots about 4.5 $\mu$m in diameter). Localization of deposited droplets using chemical or physical means, such as described in the '270 patent, is unnecessary because acoustic ejection enables precisely directed minute droplets to be deposited with accuracy at a particular site.

Figure 1:
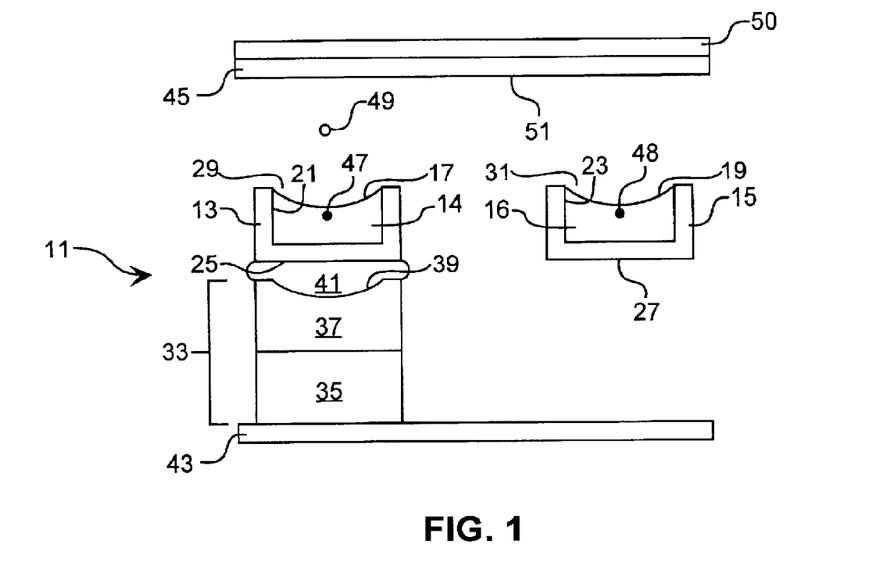
FIG. 1 shows the acoustic ejector acoustically coupled to a first reservoir and having been activated in order to eject a droplet of fluid from within the reservoir toward a particular site on a substrate surface.

FIG. 1 illustrates a suitable FAE device in simplified cross-sectional view. The device 11 generally although not necessarily includes a plurality of reservoirs, i.e., at least two reservoirs, with a first reservoir indicated at 13 and a second reservoir indicated at 15, each adapted to contain a fluid having a fluid surface, e.g., a first fluid 14 and a second fluid 16 having fluid surfaces respectively indicated at 17 and 19. Fluids 14 and 16 may the same or different. As shown, the reservoirs are of substantially identical construction so as to be substantially acoustically indistinguishable, but identical construction is not a requirement. Also, the reservoirs are shown as separate removable components but removability is not essential. For example, the plurality of reservoirs may comprise individual wells in a well plate, arranged in an array. Each of the reservoirs 13 and 15 is preferably axially symmetric, as shown, having vertical walls 21 and 23 extending upward from well bases 25 and 27 and terminating at openings 29 and 31, respectively, although other reservoir shapes may be used. The bases of each reservoir should be constructed of a material that allows acoustic radiation to be transmitted therethrough and into the fluid contained within the reservoirs. Acoustic ejector 33 includes an acoustic radiation generator 35 for generating acoustic radiation and a focusing means 37 for focusing the acoustic radiation at a focal point within the fluid and near the fluid surface from which a droplet is to be ejected. As shown in FIG. 1, the focusing means 37 may simply comprise a solid piece having a concave surface 39 for focusing acoustic radiation, but the focusing means may be constructed in other ways as well. The ejector 33 is thus adapted to generate and focus acoustic radiation so as to eject a droplet of fluid from each of the fluid surfaces 17 and 19, when acoustically coupled to reservoirs 13 and 15 and thus to fluids 14 and 16, respectively. The acoustic radiation generator 35 and the focusing means 37 may function as a single unit controlled by a single controller, or the acoustic radiation generator 35 and the focusing means 37 may be independently controlled. Optimally, acoustic coupling is achieved between the ejector and each of the reservoirs through indirect contact. FIG. 1 illustrates such acoustic coupling wherein an acoustic coupling medium 41 is placed between the surface 39 of the acoustic focusing means 37 and the base 25 of reservoir 13, with the ejector and reservoir located at a predetermined distance from each other. A preferred acoustic coupling medium is an acoustically homogeneous fluid material in conformal contact with both the acoustic focusing means 37 and each reservoir base.

In operation, reservoirs 13 and 15 are each filled with a first fluid 14 and a second fluid 16, respectively, to form fluid surfaces 17 and 19 as shown in FIG. 1. The ejector 33 is positioned by ejector positioning means 43, shown below reservoir 13, in order to achieve acoustic coupling therewith through acoustic coupling medium 41. Substrate 45 having a surface 51 for receiving ejected droplets is positioned above and in proximity to the first reservoir 13 such that one surface of the substrate, shown in FIG. 1 as underside surface 51, faces the reservoir and is substantially parallel to the surface 17 of the fluid 14 therein. Once the ejector, the reservoir and the substrate are in proper alignment, the acoustic radiation generator is activated to produce acoustic radiation that is directed by the focusing means to a focal point 47 near fluid surface 17 of the first reservoir. As a result, droplet 49 is ejected from the fluid surface 17 onto a designated site on the underside surface 51 of the substrate, forming one feature of the array.

Figure 2:
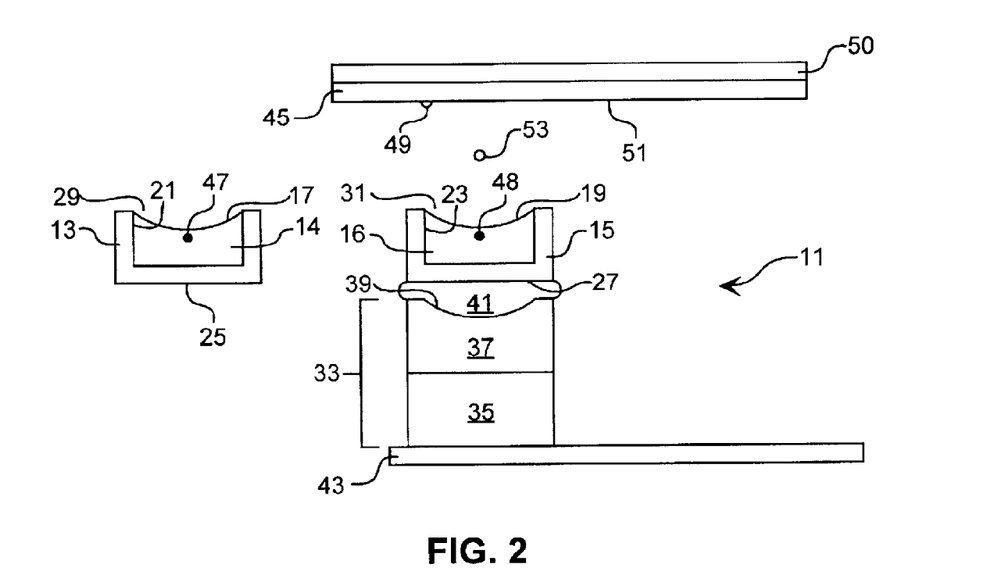
FIG. 2 shows the acoustic ejector acoustically coupled to a second reservoir.

Then, as shown in FIG. 2, a substrate positioning means 50 repositions the substrate 45 over reservoir 15, and the aforementioned process is repeated. That is, acoustic ejector 33 is repositioned by the ejector positioning means 43 below reservoir 15 so as to acoustically couple the ejector and the reservoir through acoustic coupling medium 39. Once properly aligned, the acoustic radiation generator is activated to produce acoustic radiation that is directed by the focusing means to a focal point near the fluid surface 19 from which droplet 53 is ejected onto the substrate surface 51. It will be evident to one of ordinary skill in the art that the process may be repeated to eject a plurality of fluid droplets each containing a nucleoside monomer, an intact oligonucleotide, or an oligonucleotide segment, in order to form an oligonucleotide array on a substrate surface 51.

The reservoirs used in this method may be individual wells in a well plate, e.g., a commercially available well plate containing, for example, 96, 384 or 1536 wells per well plate. Manufactures of suitable well plates include Corning Inc. (Corning, N.Y.) and Greiner America, Inc. (Lake Mary, Fla.). However, the availability of such commercially available well plates does not preclude manufacture and use of custom-made well plates containing at least about 10,000 wells, or as many as 100,000 wells or more. For array forming applications, it is expected that about 100,000 to about 4,000,000 reservoirs may be employed. In addition, to reduce the amount of movement needed to align the ejector with each reservoir or reservoir well, it is preferable that the center of each reservoir is located not more than about 1 centimeter, preferably not more than about 1 millimeter and optimally not more than about 0.5 millimeter from a neighboring reservoir center.

Other aspects of an FAE method and device that may be implemented herein are described in detail in the aforementioned Ellson et al. patent application, the disclosure of which is incorporated by reference herein.

In another embodiment, a multilayer oligonucleotide array is provided that is comprised of a plurality of identical partially nonhybridizing oligonucleotides, each of which has the formula wherein SS is a substrate surface, L is a linking moiety, $X^1$, $X^2$ and $X^3$ are hybridizing oligonucleotide segments, $Y^1$ and $Y^2$ are nonhybridizing spacer segments, m is zero or 1, and n is an integer in the range of zero to 50, wherein each nonhybridizing spacer segment $Y^i$ of each oligonucleotide is covalently linked to the corresponding nonhybridizing spacer segment $Y^i$ of at least one adjacent oligonucleotide through a linking moiety containing a cleavable site. As described above with respect to cleavable sites within the oligonucleotide backbone, the inter-oligonucleotide cleavable sites may be enzymatically, chemically, thermally, or photolytically cleavable. In this way, a ladder-type structure is provided with two or more layers of hybridizing array segments, whereby the upper array may be used first and the uppermost linking moiety then cleaved to expose the next array, and so forth. Each "array" layer may the same as the others, or each array layer may be different.

As will be appreciated by those skilled in the art, the oligonucleotides and arrays of the present invention can be used in any chemical or biochemical process involving interaction of the hybridizing segments of the partially nonhybridizing oligonucleotides with molecular species in a sample to be analyzed, e.g., in a hybridization assay to determine the presence of a particular nucleic acid analyte, in screening processes and the like. Generally, such processes are conducted by bringing the oligonucleotide array into contact with a sample that may contain a particular nucleic acid sequence, the array and sample are incubated under hybridizing conditions for a time period sufficient to allow hybridization to occur, and hybridization events, if any, are detected using conventional means, e.g., a fluorescent or enzymatic label or the like. Such procedures are in current use and will thus be known to those skilled in the art and/or described in the pertinent literature and texts.

It is to be understood that while the invention has been described in conjunction with the preferred specific embodiments thereof that the foregoing description is intended to illustrate and not limit the scope of the invention. Other aspects, advantages and modifications within the scope of the invention will be apparent to those skilled in the art to which the invention pertains. All patents, patent applications, journal articles and other references cited herein are incorporated by reference in their entireties.

The following example is put forth so as to provide those of ordinary skill in the art with a complete disclosure and description of how to implement the invention, and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE

This example describes preparation of an array of partially nonhybridizing oligonucleotides in the form of a library, and demonstrates the use of focused acoustic energy in the solid phase synthesis of partially nonhybridizing oligonucleotides.

Microporous glass, preferably controlled pore size glass (CPG), is sintered onto the surface of a glass plate to form a CPG layer having a thickness sufficient to enable permeation to both the downward flow and the lateral wicking of fluids. Generally, a sufficient thickness is greater than about 10 $\mu$m.

Accordingly, the CPG is applied to the glass surface at a thickness of about 20 $\mu$m and the glass with powdered CPG resident thereon is then heated at 750° C. for about 20 minutes and then cooled. Commercially available microscope slides (BDH Super Premium 76×26×1 mm) are used as supports. Depending on the specific glass substrate and CPG material used, the sintering temperature and time may be adjusted to obtain a permeable and porous layer that is adequately attached to the glass beneath while substantially maintaining the permeability to fluids and thickness of the microporous glass layer. The slides heated for 20 minutes with a 1 cm square patch of microporous glass applied at a pre-heating thickness of about 20 $\mu$m yield a sintered layer of substantially the same depth as pre-heating, namely 20 $\mu$m.

The microporous glass layer is derivatized with a long aliphatic linker that can withstand conditions required to deprotect the aromatic heterocyclic bases, i.e. 30% $NH_3$ at 55° C. for 10 hours. The linker, which bears a hydroxyl moiety, the starting point for the sequential formation of the oligonucleotide from nucleotide precursors, is synthesized in two steps. First, the sintered microporous glass layer is treated with a 25% solution of 3-glycidoxypropyltriethoxysilane in xylene containing several drops of Hunig's base as a catalyst in a staining jar fitted with a drying tube, for 20 hours at 90° C. The slides are then washed with MeOH, $Et_2O$ and air dried. Neat hexaethylene glycol and a trace amount of concentrated $H_2SO_4$ acid are then added and the mixture is kept at 80° C. for 20 hours. The slides are washed with MeOH, $Et_2O$, air dried and stored desiccated at −20° C. until use.

Focused acoustic ejection of about 0.24 picoliter (pL) of anhydrous acetonitrile (the primary coupling solvent) containing a fluorescent marker onto the microporous substrate is then shown to produce a circular patch of about 5.6 $\mu$m diameter on the permeable sintered microporous glass substrate. The amount of acoustic energy applied at the fluid surface may be adjusted to ensure an appropriate diameter of chemical synthesis for the desired site density. 5.6 $\mu$m diameter circular patches are suitable for preparing an array having a site density of $10^6$ sites/$cm^2$ with the circular synthetic patches spaced 10 $\mu$m apart center-to-center, and the synthetic patches therefore spaced edge-to-edge at least 4 $\mu$m apart at the region of closest proximity. All subsequent spatially directed acoustically ejected volumes in this example are of about 0.24 pL; it will be readily appreciated that the ejection volumes can be adjusted for solutions other than pure acetonitrile by adjusting the acoustic energy as necessary for delivery of an appropriately sized droplet after spreading on the substrate (here about a 5 $\mu$m radius).

The oligonucleotide synthesis cycle is performed using a coupling solution prepared by mixing equal volumes of 0.5M tetrazole in anhydrous acetonitrile with a 0.2M solution of the required β-cyanoethylphosphoramidite, e.g. A-β-cyanoethyl-phosphoramidite, C-β-cyanoethylphosphoramidite, G-β-cyanoethylphosphoramidite, T(or U)-β-cyanoethylphosphoramidite. Each oligonucleotide was synthesized with a central region of $(A)_9$, a nonhybridizing region. Coupling time is three minutes. Oxidation with a 0.1M solution of $I_2$ in THF/pyridine/$H_2O$ yields a stable phosphotriester bond. Detritylation of the 5' end with 3% trichloroacetic acid (TCA) in dichloromethane allows further extension of the oligonucleotide chain. No capping step is required because the excess of phosphoramidites used over reactive sites on the substrate is large enough to drive coupling to completion. After coupling, the subsequent chemical reactions (oxidation with $I_2$, and detritylation by TCA) are performed by dipping the slide into staining jars. Alternatively, the focused acoustic delivery of $I_2$ in THF/pyridine/$H_2O$ and/or 3% TCA in dichloromethane to effect the oxidation and tritylation steps only at selected sites may be performed if sufficient time transpires to permit evaporation of substantially all the solvent from the previous step (so that (1) the synthetic patch edges do not move outwards and closer to the neighboring synthetic patches, and (2) an anhydrous environment is provided for subsequent coupling steps).

After the synthesis is complete, the oligonucleotide is deprotected in 30% $NH_3$ for 10 hours at 55° C. Because the coupling reagents are moisture-sensitive, and the coupling step must be performed under anhydrous conditions in a sealed chamber or container. This may be accomplished by performing the acoustic spotting in a chamber of desiccated gas obtained by evacuating a chamber that contains the acoustic ejection device and synthetic substrate and replacing the evacuated atmospheric gas with desiccated $N_2$ by routine methods; washing steps may be performed in the chamber or by removing the slide and washing it in an appropriate environment, for example, by a staining jar fitted with a drying tube. Because washing and other steps such as detritylation may be more conveniently carried out outside the chamber, the synthesis may also be performed in a controlled humidity room that contains the controlled atmosphere chamber in which the spotting is done, with the other steps carried out in the room outside the chamber. Alternatively, a controlled humidity room may be used for spotting with other steps carried out in less controlled environment by use of, for example, a staining jar fitted with a drying tube.

I claim:

1. An oligonucleotide array comprised of each attached to a substrate surface through the 3'-hydroxyl group or the 5'-hydroxyl group of the oligonucleotide, wherein at least one of the oligonucleotides is a multifunctional oligonucleotide probe comprised of at least two discrete hybridizing segments with a nonhybridizing spacer segment present between any two hybridizing segments, wherein (a) at least two of the hybridizing segments within the same multifunctional oligonucleotide probe are identical, or (b) at least two of the hybridizing segments within the same multifunctional oligonucleotide probe are different and capable of hybridizing to different nucleic acid sequences, such that each hybridizing segment within the same multifunctional probe is capable of use as an individual probe, and further wherein the nonhybridizing spacer segments are selected from non-nucleotidic spacer segments and nucleotidic spacer segments having an equilibrium constant of less than or equal to 1% of the binding constant of the hybridizing segments to complementary oligonucleotide segments in an oligonucleotide analyte.

2. The oligonucleotide array of claim 1, wherein the hybridizing segments are oligonucleotide segments in the range of approximately 8 to approximately 400 nucleotides in length.

3. The oligonucleotide array of claim 2, wherein the hybridizing segments are oligonucleotide segments in the range of approximately 16 to approximately 80 nucleotides in length.

4. An oligonucleotide array comprised of a plurality of oligonucleotides attached to a substrate surface, wherein at least one of the oligonucleotides is comprised of at least two discrete hybridizing segments with a spacer segment present between any two hybridizing segments, wherein the spacer segments are oligomeric segments consisting of approximately 9 to approximately 50 identical nucleotides.

5. The oligonucleotide array of claim 4, wherein the spacer segments are comprised of $(A)_n$ wherein n is in the range of approximately 9 to approximately 50.

6. The oligonucleotide array of claim 5, wherein n is in the range of approximately 9 to approximately 20.

7. The oligonucleotide array of claim 4, wherein the spacer segments are comprised of $(T)_n$ wherein n is in the range of approximately 9 to approximately 50.

8. The oligonucleotide array of claim 7, wherein n is in the range of approximately 9 to approximately 20.

9. The oligonucleotide array of claim 4, wherein the spacer segments are comprised of $(G)_n$ wherein n is in the range of approximately 9 to approximately 50.

10. The oligonucleotide array of claim 9, wherein n is in the range of approximately 9 to approximately 20.

11. The oligonucleotide array of claim 4, wherein the spacer segments are comprised of $(C)_n$ wherein n is in the range of approximately 9 to approximately 50.

12. The oligonucleotide array of claim 11, wherein n is in the range of approximately 9 to approximately 20.

13. The oligonucleotide array of claim 4, wherein the spacer segments are comprised of $(N)_n$ wherein n is in the range of approximately 9 to approximately 50 and N is a nonnaturally occurring nucleotide or a modified naturally occurring nucleotide.

14. The oligonucleotide array of claim 13, wherein n is in the range of approximately 9 to approximately 20.

15. The oligonucleotide array of claim 1, wherein each oligonucleotide of the array is attached to the substrate surface by a covalent bond.

16. The oligonucleotide array of claim 1, wherein each oligonucleotide of the array is attached to the substrate surface by a non-covalent bond.

17. The oligonucleotide array of claim 1, wherein each oligonucleotide of the array is comprised of a multifunctional oligonucleotide probe.

18. The oligonucleotide array of claim 1, wherein each oligonucleotide of the array is different.

19. The oligonucleotide array of claim 18, wherein the hybridizing segments within any one multifunctional oligonucleotide probe are identical to each other.

20. The oligonucleotide array of claim 1, wherein the hybridizing segments within any one multifunctional oligonucleotide probe are different from each other.

21. The oligonucleotide array of claim 1, wherein the oligonucleotides of the array are comprised of a plurality of oligonucleotide groups, wherein (a) all oligonucleotides within any one group are different, and (b) each oligonucleotide group is identical to each other oligonucleotide group.

22. The oligonucleotide array of claim 1, wherein the oligonucleotides are present at a density in the range of approximately 10 to approximately 250,000 oligonucleotides per square centimeter of substrate surface.

23. The oligonucleotide array of claim 22, wherein the oligonucleotides are present at a density of at least about 1,000,000 oligonucleotides per square centimeter of substrate surface.

24. The oligonucleotide array of claim 23, wherein the oligonucleotides are present at a density of at least about 1,500,000 oligonucleotides per square centimeter of substrate surface.

25. The oligonucleotide array of claim 1, wherein the substrate surface is comprised of a porous material.

26. The oligonucleotide array of claim 25, wherein the porous material is a permeable material.

27. An oligonucleotide array comprised of a plurality of oligonucleotides, each of which has the formula $$SS\text{-}(L)_m\text{—}X^1\text{—}Y^1\text{—}X^2\text{—}(Y^2\text{—}X^3)_n,$$

wherein SS is a substrate surface, L is a linking moiety, $X^1$, $X^2$ and $X^3$ are hybridizing oligonucleotide segments, $Y^1$ and $Y^2$ are nonhybridizing spacer segments, m is zero or 1, and n is an integer in the range of zero to approximately 50, and further wherein within any one of the oligonucleotides, (a) at least two of the hybridizing segments are identical, or (b) at least two of the hybridizing segments are different and capable of hybridizing to different nucleic acid sequences, such that the oligonucleotides are capable of use as multifunctional probes, and further wherein the nonhybridizing spacer segments are selected from nonnucleotidic spacer segments and nucleotidic spacer segments having an equilibrium binding constant of less than or equal to 1% of the binding constant of the hybridizing segments to complementary oligonucleotide segments in an oligonucleotide analyte.

28. A multilayer oligonucleotide array comprised of a plurality of oligonucleotides, each of which has the formula $$SS\text{-}(L)_m\text{—}X^1\text{—}Y^1\text{—}X^2\text{—}(Y^2\text{—}X^3)_n$$

wherein SS is a substrate surface, L is a linking moiety, $X^1$, $X^2$ and $X^3$ are hybridizing oligonucleotide segments, $Y^1$ and $Y^2$ are nonhybridizing spacer segments, m is zero or 1, and n is an integer in the range of zero to 50, wherein each nonhybridizing spacer segment $Y^i$ of each oligonucleotide is covalently linked to the corresponding nonhybridizing spacer segment $Y^i$ of at least one adjacent oligonucleotide through a linking moiety containing a cleavable site, and within any one of the oligonucleotides, (a) at least two of the hybridizing segments are identical, or (b) at least two of the hybridizing segments are different and capable of hybridizing to different nucleic acid sequences, such that the oligonucleotides are capable of use as multifunctional probes, and further wherein the nonhybridizing spacer segments are selected from nonnucleotidic spacer segments and nucleotidic spacer segments having an equilibrium binding constant of less than or equal to 1% of the binding constant of the hybridizing segments to complementary oligonucleotide segments in an oligonucleotide analyte.

29. A method for synthesizing an oligonucleotide array comprised of a plurality of oligonucleotides attached to a substrate surface wherein at least one of the oligonucleotides is comprised of at least two discrete hybridizing segments with a spacer segment therebetween, wherein the spacer segment is an oligomeric segment consisting of approximately 9 to approximately 50 identical nucleotides, the method comprising: (a) providing the plurality of oligonucleotides; and (b) attaching each of the oligonucleotides to a particular location on the substrate surface.

30. The method of claim 29, wherein step (b) comprises applying each oligonucleotide to the substrate surface as a discrete fluid droplet.

31. The method of claim 30, wherein step (b) is carried out by applying focused acoustic energy to each of a plurality of fluid-containing reservoirs, each of said reservoirs containing an oligonucleotide to be applied to the substrate surface.

32. A method for synthesizing an oligonucleotide array comprised of a plurality of oligonucleotides attached to a substrate surface wherein at least one of the oligonucleotides is comprised of alternating hybridizing segments and spacer segments, wherein each spacer segment is an oligomeric segment consisting of approximately 9 to approximately 50 identical nucleotides, the method comprising successively coupling individual nucleotidic monomers and/or oligonucleotide segments to a plurality of support-bound initial nucleotidic monomers, wherein the nucleotidic monomers and/or oligonucleotide segments are selected so as to provide at least one oligonucleotide with alternating hybridizing segments and spacer segments.

33. The method of claim 32, wherein each nucleotidic monomer and/or oligonucleotide segment is applied to the substrate surface as a discrete fluid droplet.

34. The method of claim 33, wherein focused acoustic energy is applied to a fluid-containing reservoir containing the nucleotidic monomer and/or oligonucleotide segment to generate the discrete fluid droplet.

35. In a method for conducting a solid phase hybridization assay by contacting a sample with an oligonucleotide array under hybridizing conditions and thereafter detecting any hybridization events, the improvement which comprises employing the oligonucleotide array of claim 1 as the oligonucleotide array.

36. A method for synthesizing an oligonucleotide array comprised of a plurality of oligonucleotides attached to a substrate surface wherein at least one of the oligonucleotides is comprised of at least two discrete hybridizing segments with a spacer segment therebetween, the method comprising: (a) providing a plurality of fluid-containing reservoirs each containing one of the plurality of oligonucleotides; (b) applying focused acoustic energy to each of the reservoirs to eject a discrete fluid droplet from each reservoir toward a particular location on the substrate surface for deposition thereon, wherein each discrete fluid droplet contains an oligonucleotide, and further wherein the spacer segment is selected from nonnucleotidic spacer segments and nucleotidic spacer segments having an equilibrium binding constant of less than or equal to 1% of the binding constant of the hybridizing segments to complementary oligonucleotide segments in an oligonucleotide analyte.

37. A method for synthesizing an oligonucleotide array comprised of a plurality of oligonucleotides attached to a substrate surface wherein at least one of the oligonucleotides is comprised of alternating hybridizing segments and spacer segments, the method comprising successively coupling individual nucleotidic monomers and/or oligonucleotide segments to a plurality of support-bound initial nucleotidic monomers, wherein the nucleotidic monomers and/or oligonucleotide segments are selected so as to provide at least one oligonucleotide with alternating hybridizing segments and spacer segments, wherein each individual monomer and/or oligonucleotide segment is applied to the substrate as a discrete fluid droplet generated by applying focused acoustic energy to each of a plurality of fluid-containing reservoirs each containing one of said monomers and/or oligonucleotide segments, and further wherein the spacer segments are selected from nonnucleotidic spacer segments or nucleotidic spacer segments having an equilibrium binding constant of less than or equal to 1% of the binding constant of the hybridizing segments to complementary oligonucleotide segments in an oligonucleotide analyte.

38. An oligonucleotide array comprised of a plurality of multifunctional oligonucleotide probes each covalently attached through an optional linking moiety to a substrate surface through the 3'-hydroxyl group or the 5'-hydroxyl group of the probe, wherein each probe is comprised of at least two discrete hybridizing segments with a nucleotidic spacer segment present between any two hybridizing segments, wherein all hybridizing segments within the same probe are different and capable of use as individual probes and further wherein the nucleotidic spacer segment has an equilibrium binding constant of less than or equal to 1% of the binding constant of the hybridizing segments to complementary oligonucleotide segments in an oligonucleotide analyte.

* * * * *

UNITED STATES PATENT AND TRADEMARK OFFICE
CERTIFICATE OF CORRECTION

PATENT NO. : 6,806,051 B2
DATED : October 19, 2004
INVENTOR(S) : Richard N. Ellson It is certified that error appears in the above-identified patent and that said Letters Patent is hereby corrected as shown below:

<u>Column 16,</u>
Line 58, insert -- a plurality of oligonucleotide -- between the words "of" and "each"

Signed and Sealed this

Seventeenth Day of May, 2005

JON W. DUDAS
*Director of the United States Patent and Trademark Office*